United States Patent
Backhaus et al.

(10) Patent No.: US 6,410,600 B1
(45) Date of Patent: Jun. 25, 2002

(54) AZINE USED AS FUNGICIDES

(75) Inventors: Dirk Backhaus, Köln; Bernd-Wieland Krüger, Gladbach; Peter Gerdes, Aachen; Herbert Gayer, Monheim; Martin Vaupel, Leichlingen; Klaus Stenzel, Düsseldorf, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/673,758

(22) PCT Filed: Apr. 12, 1999

(86) PCT No.: PCT/EP99/02454

§ 371 (c)(1),
(2), (4) Date: Oct. 19, 2000

(87) PCT Pub. No.: WO99/55665

PCT Pub. Date: Nov. 4, 1999

(30) Foreign Application Priority Data

Apr. 23, 1998 (DE) .......................................... 198 18 313

(51) Int. Cl.⁷ ...................... A61K 31/16; C07C 251/00; C07C 229/00
(52) U.S. Cl. ........................ 514/638; 514/615; 514/640; 560/35; 560/42; 564/249
(58) Field of Search ................................. 514/638, 615, 514/640; 564/249, 294; 560/35, 42

(56) References Cited

U.S. PATENT DOCUMENTS 5,543,433 A * 8/1996 Doetzer et al. ............. 514/638

FOREIGN PATENT DOCUMENTS

| DE | 195 42 629 | | 5/1997 |
|---|---|---|---|
| EP | 0 525 516 | | 2/1993 |
| EP | 0 596 254 | | 5/1994 |
| EP | 0-596 254 | * | 5/1994 |
| EP | 0 627 411 | | 12/1994 |
| WO | 97/16415 | | 5/1997 |

OTHER PUBLICATIONS

Tetrahedron Letters, (month unavailable) 1993, pp. 5151–5154, Martin et al, Total Synthesis of The β–Methoxyacrylate based Fungicide Myxothiazol, vol. 34. No. 32 6.

* cited by examiner

*Primary Examiner*—Richard L. Raymond
*Assistant Examiner*—Sudhaker B. Patel
(74) *Attorney, Agent, or Firm*—Joseph C. Gil

(57) ABSTRACT

The invention relates to novel azines, to a process for their preparation and to their use as fungicides.

10 Claims, No Drawings

AZINE USED AS FUNGICIDES

The invention relates to novel azines, to a process for their preparation and to their use as fungicides.

It is already known that certain compounds of a similar constitution to those described below have fungicidal properties (compare, for example, EP-A 525516). However, the fungicidal action of these compounds is unsatisfactory, in particular at low application rates.

This invention, accordingly, provides the novel azines of the general formula (I)

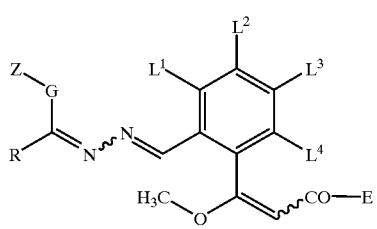

(I)

in which
E represents methoxy, ethoxy, $NH_2$ or $NH—CH_3$,
G represents a single bond or a grouping

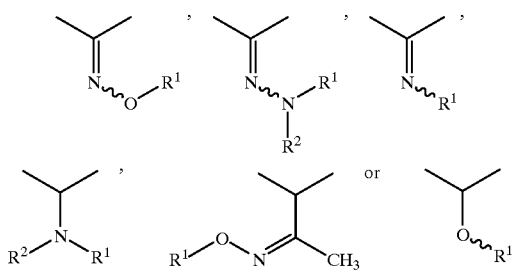

in which
$R^1$ and $R^2$ are identical or different and independently of one another each represents optionally substituted alkyl, alkenyl, alkinyl, aryl, cycloalkyl, alkylcarbonyl or arylcarbonyl, or
$R^1$ and $R^2$ together with the nitrogen atom to which they are attached form a saturated or unsaturated heterocyclic ring,
R represents hydrogen, alkyl or in each case optionally substituted cycloalkyl or aryl,
Z represents cyano, alkoxycarbonyl, alkoxy, cycloalkoxy or in each case optionally substituted alkyl, cycloalkyl, cycloalkylalkyl, aryl, arylalkyl, heterocyclyl or heterocyclylalkyl and
$L^1$, $L^2$, $L^3$ and $L^4$ are identical or different and independently of one another each represents hydrogen, halogen, cyano, nitro, in each case optionally halogen-substituted alkyl, alkoxy, alkylthio, alkylsulphinyl or alkylsulphonyl.

In the definitions, the saturated or unsaturated hydrocarbon chains, such as alkyl, are in each straight-chain or branched, including in combination with hetero atoms, such as in alkoxy or alkylthio.

Halogenoalkyl represents partially or fully halogenated alkyl. In the case of polyhalogenated halogenoalkyl, the halogen atoms can be identical or different. Preferred halogen atoms are fluorine and in particular fluorine. If the halogenoalkyl carries further substituents, the maximum possible number of the halogen atoms is reduced to the remaining free valencies.

Halogen generally represents fluorine, chlorine, bromine or iodine, preferably fluorine, chlorine or bromine, in particular fluorine or chlorine.

Heterocyclyl represents saturated or unsaturated, and also aromatic, cyclic compounds in which at least one ring member is a hetero atom, i.e. an atom different from carbon. If the ring contains a plurality of hetero atoms, these can be identical or different. Preferred hetero atoms are oxygen, nitrogen or sulphur. If the ring contains a plurality of oxygen atoms, these are not adjacent. If appropriate, the cyclic compounds form, together with further carbocyclic or heterocyclic, fused-on or bridged rings, a polycyclic ring system. A polycyclic ring system can be attached via the heterocyclic ring or a fused-on carbocyclic ring. Preference is given to mono- or bicyclic ring systems, in particular mono- or bicyclic, aromatic ring systems.

Benzoheterocyclyl as a sub-group of heterocyclyl represents heterocyclyl which is fused to a phenyl ring.

Dibenzoheterocyclyl represents heterocyclyl which is fused to two phenyl rings.

Furthermore, it has been found that the novel azines of the general formula (I) are obtained when hydrazones of the formula (II)

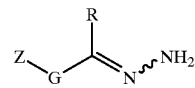

(II)

in which
G, R and Z are as defined above are reacted with an aldehyde of the general formula (III)

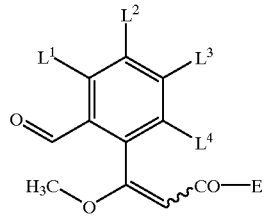

(III)

in which
E, $L^1$, $L^2$, $L^3$ and $L^4$ are as defined above,
if appropriate in the presence of a diluent and if appropriate in the presence of a catalyst.

Finally, it has been found that the novel azines of the general formula (I) have very strong fungicidal activity.

Compounds of the formula (I) in which E represents amino or methylamino can also be prepared in a simple manner from compounds of the formula (I) in which E represents methoxy or ethoxy, by reaction with ammonia, or methylamine, if appropriate in the presence of a diluent (compare also Tetrahedron Letters 1993, 5151–5154).

The compounds according to the invention can, if appropriate, be present as mixtures of different possible isomeric forms, in particular of stereoisomers, such as, for example, E and Z, or optical isomers. What is claimed are both the E and the Z isomers, the individual enantiomers, the racemates, and any mixtures of these isomers.

Preference is given to azines of the formula (I), in which
E represents methoxy, ethoxy, $NH_2$ or $NH—CH_3$, in particular methoxy, G represents a single bond, R represents alkyl having 1 to 4 carbon atoms or represents cycloalkyl having 3 to 6 carbon atoms or phenyl, each of which is optionally mono- to tetrasubstituted by halogen or alkyl, and in particular represents methyl or cyclopropyl, Z represents cycloalkyl or cycloalkylalkyl having in each case 3 to 7 carbon atoms in the cycloalkyl moiety and 1 to 4 carbon atoms in the alkyl moiety and being in each case optionally mono- to tetrasubstituted by halogen or alkyl; or represents heterocyclyl, benzoheterocyclyl, dibenzoheterocyclyl or hetero-cycloalkyl having in each case 3 to 7 ring members in the heterocyclyl moiety and 1 to 4 carbon atoms in the alkyl moiety and being optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms or phenyl;

or represents aryl or arylalkyl having in each case 6 to 10 carbon atoms in the aryl moiety and 1 to 4 carbon atoms in the alkyl moiety and being in case optionally mono- to tetrasubstituted in the aryl moiety by identical or different substituents, where the possible substituents are preferably selected from the list below:

halogen, cyano, nitro, amino, carbamoyl, thiocarbamoyl;

in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkoxycarbonyl, alkylaminocarbonyl, dialkylaminocarbonyl or arylalkylaminocarbonyl having 1 to 6 carbon atoms in the respective hydrocarbon chains;

cycloalkyl or cycloalkyloxy having in each case 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents from the group consisting of fluorine, chlorine, methyl, trifluoromethyl and ethyl;

phenoxy or phenylalkoxy having 1 to 4 carbon atoms in the alkyl moiety, each of which is optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms, heterocyclyl, heterocyclyloxy, heterocyclylthio, heterocyclylsulphinyl or heterocyclylsulphonyl having 5 or 6 ring members, each of which is optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms or phenyl, or a grouping

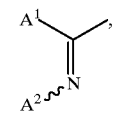

in which $A^1$ represents hydrogen or alkyl having 1 to 4 carbon atoms or cycloalkyl having 3 to 6 carbon atoms and $A^2$ represents hydroxyl, amino, methylamino, methyl, phenyl, benzyl, alkoxy, alkylamino, dialkylamino having 1 to 4 carbon atoms in the respective alkyl chains and $L^1$, $L^2$, $L^3$ and $L^4$ are identical or different and independently of one another each represents hydrogen, halogen, cyano, nitro, or alkyl, alkoxy, alkylthio, alkylsulphinyl or alkylsulphonyl having in each case 1 to 6 carbon atoms and being in each case optionally substituted by 1 to 5 halogen atoms, and preferably represents hydrogen or methyl and in particular hydrogen.

Preference is also given to azines of the formula (I), in which

E represents methoxy, ethoxy, $NH_2$ or $NH-CH_3$, in particular methoxy,

G represents a grouping

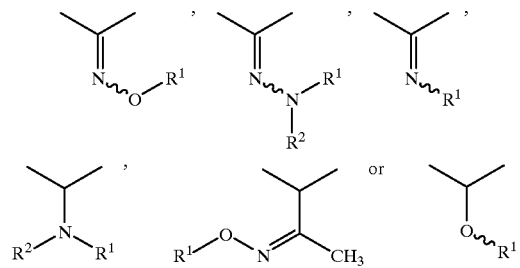

in which $R^1$ and $R^2$ are identical or different and independently of one another represent alkinyl having 2 to 6 carbon atoms, alkenyl having 2 to 6 carbon atoms or alkyl or alkylcarbonyl having 1 to 6 carbon atoms, each of which is optionally substituted by halogen or alkoxy having 1 to 4 carbon atoms, or represents cycloalkyl having 3 to 8 carbon atoms which is optionally substituted by halogen, alkyl or alkoxy having in each case 1 to 4 carbon atoms or represents phenyl, heteroaryl, heteroarylalkyl or phenylalkyl having optionally 1 to 4 carbon atoms in the alkyl moiety or phenylcarbonyl, each of which is optionally substituted in the phenyl moiety or heteroaryl moiety, where the substituents are selected from the list below:

halogen, cyano, nitro, alkyl, alkoxy, alkylthio, alkylsulphinyl or alkylsulphonyl having in each case 1 to 6 carbon atoms, halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case halogenoalkyl or halogenoalkyloxy having in each case 2 to 6 carbon atoms and 1 to 11 identical or different halogen atoms, or $R^1$ and $R^2$ together with the nitrogen atom to which they are attached form a saturated or unsaturated heterocyclic ring having 5 or 6 ring members, R represents alkyl having 1 to 4 carbon atoms or represents cycloalkyl having 3 to 6 carbon atoms or phenyl, each of which is optionally mono- to tetra-substituted by halogen or alkyl, Z represents cyano, alkoxycarbonyl or alkoxy having in each case 1 to 4 carbon atoms in the alkyl moiety, cycloalkoxy having 5 or 6 carbon atoms, or represents alkyl or halogenoalkyl having in each case 1 to 4 carbon atoms and being in each case optionally monosubstituted by cyano or alkoxy, or represents cycloalkyl or cycloalkylalkyl having in each case 3 to 7 carbon atoms in the cycloalkyl moiety and 1 to 4 carbon atoms in the alkyl moiety and being in each case optionally mono- to tetrasubstituted by halogen or alkyl; or represents heterocyclyl, benzoheterocyclyl, dibenzoheterocyclyl or heterocyclyl alkyl having in each case 3 to 7 ring members in the heterocyclyl moiety and 1 to 4 carbon atoms in the alkyl moiety and being optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms or phenyl;

or represents aryl or arylalkyl having in each case 6 to 10 carbon atoms in the aryl moiety and 1 to 4 carbon atoms in the alkyl moiety and being in each case optionally mono- to tetrasubstituted in the aryl moiety by identical or different substituents, where the possible substituents are preferably selected from the list below:

halogen, cyano, nitro, amino, carbamoyl, thiocarbamoyl;

in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkoxycarbonyl, alkylaminocarbonyl, dialkylaminocarbonyl or arylalkylaminocarbonyl having 1 to 6 carbon atoms in the respective hydrocarbon chains;

cycloalkyl or cycloalkyloxy having in each case 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents from the group consisting of fluorine, chlorine, methyl, trifluoromethyl and ethyl;

phenoxy or phenylalkoxy having 1 to 4 carbon atoms in the alkyl moiety, each of which is optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms, heterocyclyl, heterocyclyloxy, heterocyclylthio, heterocyclylsulphinyl or heterocyclylsulphonyl having 5 or 6 ring members, each of which is optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms or phenyl, or a grouping

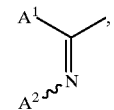

in which $A^1$ represents hydrogen or alkyl having 1 to 4 carbon atoms or cycloalkyl having 3 to 6 carbon atoms and $A^2$ represents hydroxyl, amino, methylamino, methyl, phenyl, benzyl, alkoxy, alkylamino, dialkylamino having 1 to 4 carbon atoms in the respective alkyl chains and $L^1$, $L^2$, $L^3$ and $L^4$ are identical or different and independently of one another each represents hydrogen, halogen, cyano, nitro, or alkyl, alkoxy, alkylthio, alkylsulphinyl or alkylsulphonyl having in each case 1 to 6 carbon atoms and being in each case optionally substituted by 1 to 5 halogen atoms, and preferably represents hydrogen or methyl and in particular hydrogen.

Particular preference is given to azines of the formula (I), in which

E represents methoxy, ethoxy, amino or methylamino, in particular represents methoxy, G represents a single bond, R represents methyl, ethyl, n- or i-propyl, or represents cyclopropyl, cyclobutyl, cyclopentyl or phenyl, each of which is optionally mono- to tetrasubstituted by fluorine, chlorine, methyl or ethyl; and in particular represents methyl or cyclopropyl, Z represents cyclopentyl or cyclohexyl, each of which is optionally mono- to tetrasubstituted by fluorine, chlorine, methyl or ethyl; or represents pyridyl, furyl, piperazinyl, thiazolyl, dioxazinyl, benzimidazolyl, benzothiazolyl, benzofuranyl, benzopyrazolyl, dibenzothiazinyl, thienylmethyl, pyridylmethyl, furylmethyl or thienyl, optionally substituted by methyl, ethyl, fluorine, chlorine, bromine, trifluoromethyl, phenyl;
or represents benzyl, 1-phenylethyl or 2-phenylethyl, each of which is optionally mono- to tetrasubstituted by identical or different substituents, and in particular represents substituted phenyl, where the possible substituents are preferably selected from the list below:
  fluorine, chlorine, bromine, cyano, nitro, amino, carbamoyl, thiocarbamoyl, methyl, ethyl, n- or i-propyl, n-, i-, s- or t-butyl, methoxymethyl, methoxy, ethoxy, n- or i-propoxy,
  methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;
  trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, methoxycarbonyl, ethoxycarbonyl, methylaminocarbonyl, ethylaminocarbonyl, dimethylaminocarbonyl, diethylaminocarbonyl, cyclopentyl, cyclohexyl, cyclopentyloxy, cyclohexyloxy,
  in each case doubly attached propanediyl, ethyleneoxy, methylenedioxy, ethylenedioxy, each of which is optionally mono- to tetrasubstituted by identical or different substituents from the group consisting of fluorine, chlorine, methyl and trifluoromethyl
in each case optionally fluorine-, chlorine-, methyl-, trifluoromethyl- or methoxy-substituted phenoxy or benzyl,
  heterocyclyl, heterocyclyloxy, heterocyclylthio, heterocyclylsulphinyl or heterocyclylsulphonyl having 5 or 6 ring members and being in each case optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms or phenyl,
  represents optionally methyl-, ethyl-, fluorine-, chlorine-, bromine-, trifluoromethyl-, phenyl-substituted thienyl, imidazolyl, thiadiazolyl, pyridyl, furyl, piperazinyl, thiazolyl, dioxazinyl, thiadiazolylsulphonyl;
  or a grouping

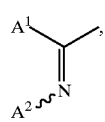

where
    $A^1$ represents hydrogen or methyl and
    $A^2$ represents hydroxyl, methoxy, ethoxy, amino, methylamino, methyl, phenyl or benzyl, and $L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, preferably represents hydrogen or methyl and in particular represents hydrogen.

Particular preference is also given to azines of the formula (I), in which
  E represents methoxy, ethoxy, amino or methylamino, and in particular represents methoxy,
  G represents a grouping

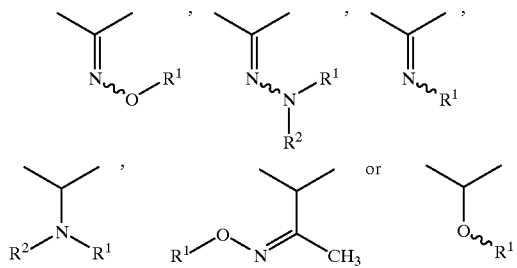

, in which
  $R^1$ and $R^2$ are identical or different and independently of one another each represents in each case optionally fluorine-, chlorine- or methoxy-substituted methyl, ethyl, n- or i-propyl, n-, i-, s- or t-butyl, acetyl, propionyl, allyl, crotonyl, propargyl or represents optionally fluorine-, chlorine-, methyl- or methoxy-substituted cyclopentyl or cyclohexyl or represents phenyl, benzyl, pyridylmethyl or benzoyl, each of which is optionally substituted in the phenyl moiety, where the substituents are selected from the list below:
    fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl,
  $R^1$ and $R^2$ together with the nitrogen atom to which they are attached form a pyrrole, pyrrolidine, imidazole or triazole ring,
R represents methyl, ethyl, n- or i-propyl, or represents cyclopropyl, cyclobutyl, cyclopentyl or phenyl, each of which is optionally mono- to tetrasubstituted by fluorine, chlorine, methyl or ethyl,
Z represents cyano, methoxycarbonyl, ethoxycarbonyl, methyl, ethyl, n- or i-propyl, n-, i-, s- or t-butyl, trifluoromethyl, trifluoroethyl, methoxy, ethoxy, n- or i-propoxy, cyclopentyloxy or cyclohexyloxy or
  represents cyclopentyl or cyclohexyl, each of which is optionally mono- to tetrasubstituted by fluorine, chlorine, methyl or ethyl; or represents pyridyl, furyl, piperazinyl, thiazolyl, dioxazinyl, benzimidazolyl, benzothiazolyl, benzofuranyl, benzopyrazolyl, dibenzothiazinyl, thienylmethyl, pyridylmethyl, furylmethyl or thienyl, optionally substituted by methyl, ethyl, fluorine, chlorine, bromine, trifluoromethyl, phenyl;

or represents benzyl, 1-phenylethyl or 2-phenylethyl, each of which is optionally mono- to tetrasubstituted by identical or different substituents, and in particular represents substituted phenyl, where the possible substituents are preferably selected from the list below:

fluorine, chlorine, bromine, cyano, nitro, amino, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

trifluoromethyl, trifluoroethyl, difluoromethoxy, trifluoromethoxy, difluorochloromethoxy, trifluoroethoxy, pentafluoroethoxy, 2-chloro-1,1, 2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, methoxycarbonyl, ethoxycarbonyl, methylaminocarbonyl, ethylaminocarbonyl, dimethylaminocarbonyl, diethylaminocarbonyl, cyclopentyl, cyclohexyl, cyclopentyloxy, cyclohexyloxy, in each case doubly attached propanediyl, ethyleneoxy, methylenedioxy, ethylenedioxy, each of which is optionally mono- to tetrasubstituted by identical or different substituents from the group consisting of fluorine, chlorine, methyl and trifluoromethyl in each case optionally fluorine-, chlorine-, methyl-, trifluoromethyl- or methoxy-substituted phenoxy or benzyl, heterocyclyl, heterocyclyloxy, heterocyclylthio, heterocyclylsulphinyl or heterocyclylsulphonyl having 5 or 6 ring members and being in each case optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms or phenyl, represents optionally methyl-, ethyl-, fluorine-, chlorine-, bromine-, trifluoromethyl-, phenyl-substituted thienyl, imidazolyl, thiadiazolyl, pyridyl, furyl, piperazinyl, thiazolyl, dioxazinyl, thiadiazolylsulphonyl;

or a grouping

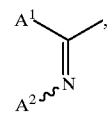

where $A^1$ represents hydrogen or methyl and $A^2$ represents hydroxyl, methoxy, ethoxy, amino, methylamino, methyl, phenyl or benzyl, and $L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methyl-thio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethythio, trifluoromethylthio, trifluoromethylsulphinyl or trifluoromethylsulphonyl, preferably represents hydrogen or methyl and in particular represents hydrogen.

Preference is given to compounds in which $L^1$, $L^2$, $L^3$, $L^4$ represent hydrogen, Preference is given to compounds in which R represents methyl. Preference is given to compounds in which G represents C=N—$OR^1$.

The abovementioned general or preferred radical definitions apply both to the end products of the formula (I) and, correspondingly, to the starting materials or intermediates required in each case for the preparation.

These radical definitions can be combined with one another as desired, i.e. including combinations between the given ranges of preferred compounds.

The formula (II) provides a general definition of the hydrazones required as starting materials for carrying out the process according to the invention. In this formula (II), G, R and Z preferably or in particular have those meanings which have already been mentioned in connection with the description of the compounds of the formula (I) according to the invention as being preferred or as being particularly preferred for G, R and Z.

The hydrazones of the formula (II) are known or can be prepared from the corresponding ketones and hydrazine by customary standard methods.

The formula (III) provides a general definition of the aldehydes furthermore required as starting materials for carrying out the process according to the invention. In this formula (III), E, $L^1$, $L^2$, $L^3$ and $L^4$ preferably or in particular have those meanings which have already been mentioned in connection with the description of the compounds of the formula (I) according to the invention as being preferred or as being particularly preferred for E, $L^1$, $L^2$, $L^3$ and $L^4$.

The aldehydes of the formula (E) are known and can be prepared by known methods (compare EP-A 525516).

Suitable diluents for carrying out the process according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl-t-amyl ether, dioxane, tetrahydrofuran, 1,2- dimethoxyethane, 1,2-diethoxyethane or anisole; sulphoxides, such as dimethyl sulphoxide; sulphones, such as sulpholane; or alcohols, such as methanol, ethanol, n- or i-propanol, n-, i-, sec- or tert-butanol, ethanediol, propane- 1,2-diol, ethoxyethanol, methoxyethanol, diethylene glycol monomethyl ether or diethylene glycol monoethyl ether.

The process according to the invention is, if appropriate, carried out in the presence of a catalyst. Suitable catalysts are inorganic and organic acids. These include, for example, sulphuric acid, phosphoric acid, formic acid, trifluoroacetic acid, methanesulphonic acid, trifluoromethanesulphonic acid, toluenesulphonic acid, acidic ion exchangers, acidic alumina and acidic silica gel.

When carrying out the process according to the invention, the reaction temperatures can be varied within a relatively wide range. In general, the process is carried out at temperatures from 20° C. to 180° C., preferably at temperatures from 20° C. to 150° C.

For carrying out the process according to the invention for preparing the compounds of the formula (I), in general from 0.5 to 2 mol, preferably from 0.8 to 1.5 mol, of aldehyde of the formula (III) are employed per mole of hydrazone of the formula (II).

The process according to the invention is generally carried out under atmospheric pressure. However, it is also possible to operate under elevated or reduced pressure—in general between 0.1 bar and 10 bar.

The practice of the reaction and the work-up and isolation of the reaction products are carried out by generally customary methods (compare also the Preparation Examples).

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Bottytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in fruit and vegetable growing and viticulture, such as, for example, against Venturia, Sphaerotheca, and Plasmopara species.

The active compounds according to the invention may also be employed to increase the yield of crops. Moreover, they have a low toxicity and are tolerated well by plants.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discoloring and wood-destroying fungi (Basidiomycetes) and against slime organisms and algae.

Microorganisms of the following genera may be mentioned as examples:

Altemaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*, and
Staphylococcus, such as *Staphylococcus aureus*.

Depending on their particular physical and/or chemical properties, the active compounds can be converted to the customary formulations, such as solutions, emulsions, suspensions, powders, foams, pastes, granules, aerosols and micro-encapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, 1-isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethybenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano-[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholinehydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)4-methyl-3-nitro-benzenesulphonamide, N-(4-cyclohexylphenyl)-3,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides:
bromopol, dichlorophen, nitrapyrin, nickel dimethyldithiocarbamate, kasugamycin, octhilinone, flurancarboxylic acid, oxytetracyclin, probenazole, streptomycin, tecloftalam, copper sulphate and other copper preparations.

Insecticides/Acaricides/Nematicides:
abamectin, acephate, acrinathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chlorophenyl)-1-(ethoxymethyl)-5-(tri-fluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth-promoting substances.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the active compound application rates are, in general, between 0.1 and 10,000 g/ha, preferably between 10 and 1000 g/ha. In the treatment of seed, the active compound application rates are generally between 0.001 and 50 g per kilogram of seed, preferably between 0.01 and 10 g per kilogram of seed. In the treatment of the soil, the active compound application rates are generally between 0.1 and 10,000 g/ha, preferably between 1 and 5000 g/ha.

The compositions used for protecting industrial materials generally comprise the active compounds in an amount of from 1 to 95%, preferably from 10 to 75%.

The use concentrations of the active compounds according to the invention depend on the nature and the occurrence of the microorganisms to be controlled and on the composition of the material to be protected. The optimum application rate can be determined by test series. In general, the use concentrations are in the range of from 0.001 to 5% by weight, preferably from 0.05 to 1.0% by weight, based on the material to be protected.

The activity and the activity spectrum of the active compounds to be used according to the invention in the protection of materials, or of the compositions, concentrates or quite generally formulations prepared therefrom, can be increased by adding, if appropriate, other antimicrobially active compounds, fungicides, bactericides, herbicides, insecticides or other active compounds to widen the activity spectrum or to obtain particular effects, such as, for example, additional protection against insects. These mixtures may have a broader activity spectrum than the compounds according to the invention.

PREPARATION EXAMPLES

Example (1)

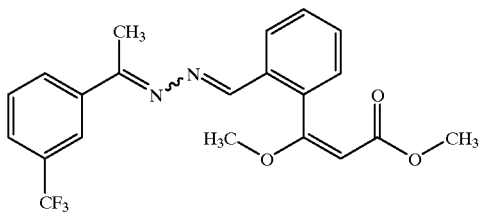

0.2 g (0.9 mmol) of methyl 3-(2-formylphenyl)-3-methoxyacrylate, 0.29 g (1.09 mmol) of 3-trifluoromethylacetophenone hydrazone and 1 g of pulverized molecular sieve in 5 ml of dichloromethane are stirred at 20° C. for 18 hours. The reaction mixture is filtered and the filtrate is concentrated under reduced pressure. The residue is chromatographed with cyclohexane/ethyl acetate (2:1) over silica gel. This gives 0.20 g (56.1% of theory) of methyl 3-methoxy-3-(2-{[1-(3-trifluoromethylphenyl)-ethylidene]-hydrazonomethyl}-phenyl)-acrylate.

HPLC: logP=4.40

The compounds of the formula (I-a) according to the invention listed in Table 1 below are also obtained analogously to Example (1), and in accordance with the general description of the preparation process according to the invention:

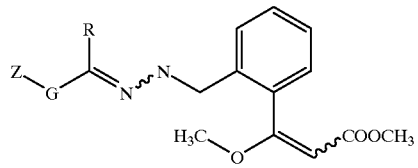

(I-a)

TABLE 1

| Example | G | R | Z | phys. data |
|---|---|---|---|---|
| 2 | — | —CH₃ | 4-dimethylaminophenyl | |
| 3 | — | —CH₃ | 2.4-dimethoxyphenyl | |
| 4 | — | —CH₃ | 2.4-difluorophenyl | |
| 5 | — | —CH₃ | 2.4-dichlorophenyl | |
| 6 | — | —CH₃ | ![structure: 4-methylphenyl-O-CF₂-CHFCl] | |
| 7 | — | —CH₃ | 4-(2-chloro-6-fluoro-4-trifluoromethylphenoxy)-phenyl | |
| 8 | — | —CH₃ | 4-trifluoromethylphenyl | |
| 9 | — | —CH₃ | 4-trifluoromethoxyphenyl | |
| 10 | — | —CH₃ | ![structure: 4-(imidazol-1-yl)-methylphenyl] | |
| 11 | — | —CH₃ | ![structure: methyl-benzodioxole] | |
| 12 | — | —CH₃ | 4-(i-propyl)phenyl | |
| 13 | — | —CH₃ | 3-tolyl | |
| 14 | — | —CH₃ | 3-chlorophenyl | |
| 15 | — | —CH₃ | 4-ethylphenyl | |
| 16 | — | —CH₃ | 3-bromophenyl | |
| 17 | — | —CH₃ | 3-trifluoromethoxyphenyl | |
| 18 | — | —CH₃ | 4-difluoromethoxyphenyl | |
| 19 | — | —CH₃ | ![structure: 2-chloro-5-methylpyridine] | |

TABLE 1-continued

| Example | G | R | Z | phys. data |
|---|---|---|---|---|
| 20 | — | —CH₃ | 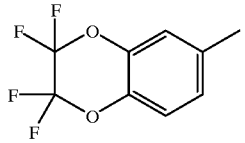 | |
| 21 | — | —CH₃ | 4-cyanophenyl | |
| 22 | — | —CH₃ | 3.4-dichlorophenyl | |
| 23 | — | —H | 3-trifluoromethylphenyl | |
| 24 | — | —CH₃ | 3-cyanophenyl | |
| 25 | — | cyclopropyl | 4-chlorophenyl | |
| 26 | — | —CH₃ | 4-methoxy-3-nitrophenyl | logP** = 3.7(n) NMR*: 3.53(s); 3.86(s); 4.02(s); 5.48(s) |
| 27 | — | —CH₃ | 3-benzyloxyphenyl | |
| 28 | — | —CH₃ | 4-(2,6-dichloro-benzyloxy)-phenyl | |
| 29 | 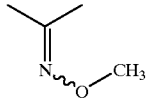 | —CH₃ | phenyl | |
| 30 | — | —CH₃ | 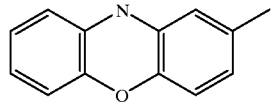 | |
| 31 | — | —CH₃ | 4-trifluoromethylthio-phenyl | |
| 32 | — | —CH₃ | 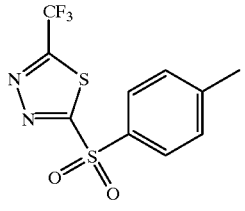 | |
| 33 | — | —CH₃ | 4-trifluoromethylsul-phonylphenyl | logP** = 4.2(n) NMR*: 3.53(s); 3.85(s); 5.48(s) |
| 34 | — | —CH₃ | 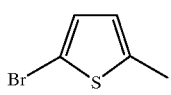 | |
| 35 | 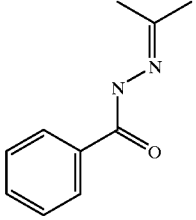 | —CH₃ | —CH₃ | |

TABLE 1-continued

| Example | G | R | Z | phys. data |
|---|---|---|---|---|
| 36 | (propan-2-ylidene)(cyclohexyl)amine | —CH₃ | cyclohexyloxy | |
| 37 | 1-isopropyl-1,2,4-triazole | —CH₃ | —OCH₃ | |
| 38 | (propan-2-ylidene)-O-methyl oxime | —CH₃ | —COOCH₃ | |
| 39 | (propan-2-ylidene)-O-methyl oxime | —CH₃ | —COOC₂H₅ | |
| 40 | — | —CH₃ | 2-benzothiazolyl | |
| 41 | — | —CH₃ | 2,4,5-trimethylthiazol-2-yl | |
| 42 | — | —CH₃ | 5-chloro-2-methylthiophen-2-yl | |
| 43 | — | —CH₃ | piperazinyl | |
| 44 | — | —CH₃ | 2-methylthiazol-2-yl | |
| 45 | — | —CH₃ | 2-pyridyl | |
| 46 | — | —CH₃ | 3-methyl-2-ethylpyrazinyl | |
| 47 | — | —CH₃ | 2,3-dimethylpyrazinyl | |

TABLE 1-continued
| Example | G | R | Z | phys. data |
|---|---|---|---|---|
| 48 | — | —CH₃ | 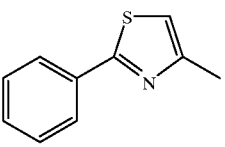 | |
| 49 | — | —CH₃ | 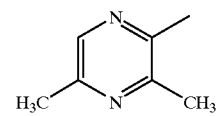 | |
| 50 |  | —CH₃ | phenyl | |
| 51 | 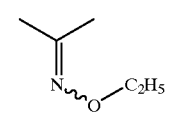 | —CH₃ | —CH₃ | logP** = 4.3(s)<br>NMR*: 3.52(s);<br>3.82(s);<br>5.44(s); 8.12(s) |
| 52 | 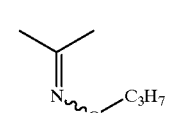 | —CH₃ | —CH₃ | logP** = 4.8(s)<br>NMR*: 3.52(s);<br>3.82(s);<br>5.44(s); 8.12(s) |
| 53 | 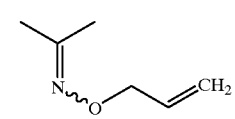 | —CH₃ | —CH₃ | logP** = 4.4(s)<br>NMR*: 3.52(s);<br>3.82(s);<br>5.44(s); 8.13(s) |
| 54 | 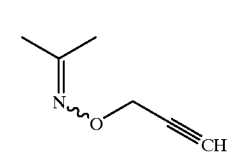 | —CH₃ | —CH₃ | logP** = 3.8(s)<br>NMR*: 3.82s);<br>5.44(s); 8.11(s) |
| 55 | 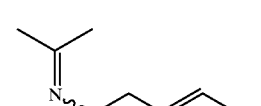 | —CH₃ | —CH₃ | NMR*: 3.52(s);<br>3.82(s);<br>5.43(s); 8.11(s) |
| 56 | — | —H | 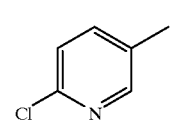 | |
| 57 | — | —CH₃ | 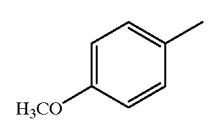 | NMR*: 3.82(s);<br>3.88(s);<br>5.45(s); 8.37(s) |
| 58 | — | —CH₃ | 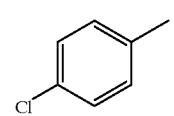 | NMR*: 3.52(s);<br>3.83(s);<br>5.45(s); 8.38(s) |

TABLE 1-continued

| Example | G | R | Z | phys. data |
|---|---|---|---|---|
| 59 | — | —CH₃ | 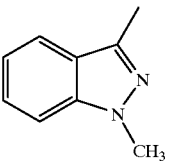 | NMR*: 3.53(s); 3.86(s); 5.48(s); 8.45(s) |
| 60 | — | —CH₃ | 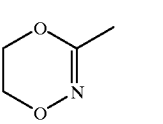 | logP** = 2.4(n) NMR*: 3.51(s); 3.81(s); 5.42(s); 8.30(s) |
| 61 | 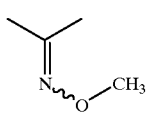 | —CH₃ | —CH₃ | logP** = 3.8(n) NMR*: 3.52(s); 4.01(s); 5.44(s); 8.12(s) |
| 62 | 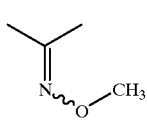 | —CH₃ | -i-propyl | logP** = 4.4(n) NMR*: 3.52(s); 3.96(s); 5.44(s); 8.09(s) |
| 63 | 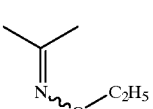 | —CH₃ | -i-propyl | logP** = 5.05(s) |
| 64 | 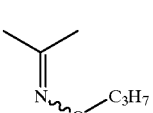 | —CH₃ | -i-propyl | logP** = 5.51(s) |
| 65 | 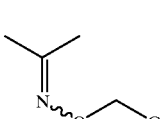 | —CH₃ | -i-propyl | logP** = 5.43(s) |
| 66 | 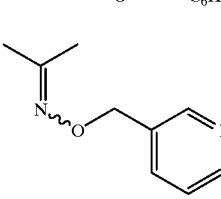 | —CH₃ | -i-propyl | logP** = 4.76(s) |
| 67 | 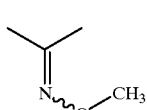 | —CH₃ | -ethyl | logP** = 4.25(s) |

*The ¹H-NMR spectra were recorded in deuterochloroform (CDCl₃) or hexa-deuterodimethylsulphoxide (DMSO-d₆) using tetramethylsilane (TMS) as internal standard. What is stated in the chemical shift as δ value in ppm.
**The logP values were determined in accordance with EEC direction 79/831 Annex V. A8 by HPLC (gradient method, acetonitrile/0.1% aqueous phosphoric acid(s) or gradient method, acetonitrile/0.1% water (n))

Preparation of Starting Materials (exemplary)

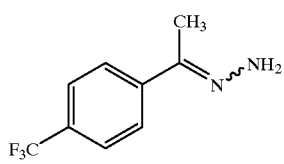

24.5 g (0.13 mole) of 4-trifluoromethylacetophenone and 26 g (0.52 mol) of hydrazine hydrate in 100 ml of methanol are heated under reflux for 1.5 hours. After cooling, the mixture is poured into 800 ml of water and extracted three times with in each case 200 ml of dichloromethane. The organic phase is separated off, dried over magnesium sulphate and concentrated under reduced pressure. This gives 23.5 g (89% of theory) of 4-trifluoromethylacetophenone hydrazone.

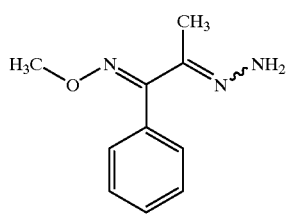

2.5 g (0.014 mol) of 1-phenylpropane-1,2-dione 1-(O-methyl oxime) (Chem Ber. 40, 1907, 1624; Chem Ber. 38, 1905, 1919; J. Chem. Soc. 11, 1991, 1809–1818) in 20 ml of ethanol are heated with 1.45 g (0.029 mol) of hydrazine hydrate at 60° C. for 1 hour. The reaction mixture is poured into water, extracted with diethyl ether, the organic phase is dried over sodium sulfate and the solvent is distilled off under reduced pressure. The residue is stirred with diethyl ether and the crystals are filtered off. This gives 1.5 g (55.6% of theory) of 2-hydrazono-1-phenylpropan-1-one O-methyl oxime of melting point 132° C.

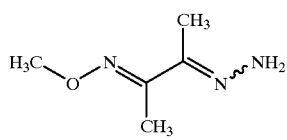

3 g (0.026 mol) of butane-2,3-dione mono-(O-methyl oxime) in 20 ml of ethanol are heated with 2.6 g (0.052 mol) of hydrazine hydrate at 60° C. for 1 hour. The reaction mixture is poured into water, extracted with diethyl ether, the organic phase is dried over sodium sulphate and the solvent is distilled off under reduced pressure. The residue is stirred with petroleum ether and the crystals are filtered off. This gives 1 g (29.7% of theory) of 3-hydrazono-butan-2-one O-methyl oxime.

HPLC: logP =0.97.

$^1$H-NMR spectrum (DMSO-d6/TMS): δ=1.81 (3H); 1.91 (3H); 3.83 (3H); 6.73 (2H, NH$_2$) ppm.

USE EXAMPLES

Example A
Plasmopara Test (grapevine)/Protective

| | |
|---|---|
| Solvent: | 47 parts by weight of acetone |
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Plasmopara viticola and then remain in an incubation cabin at approximately 20° C. and 100% relative atmospheric humidity for 1 day. The plants are then placed in a greenhouse at approximately 21° C. and approximately 90% relative atmospheric humidity. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the substance according to the invention listed in Example (1) exhibits, at an application rate of 100 g/ha, an efficacy of more than 80%.

Example B
Sphaerotheca Test (cucumber)/Protective

| | |
|---|---|
| Solvent: | 47 parts by weight of acetone |
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

In this test, the substance according to the invention listed in Example (1) exhibits, at an application rate of 100 g/ha, an efficacy of more than 80%.

Example C
Venturia Test (apple)/Protective

| | |
|---|---|
| Solvent: | 47 parts by weight of acetone |
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab Venturia inaequalis and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, whereas an efficacy of 100% means that no infection is observed.

In this test, the substance according to the invention listed in example (1) exhibits, at an application rate of 10 g/ha, an efficacy of more than 90%.

What is claimed is:

1. Compounds of the formula (I)

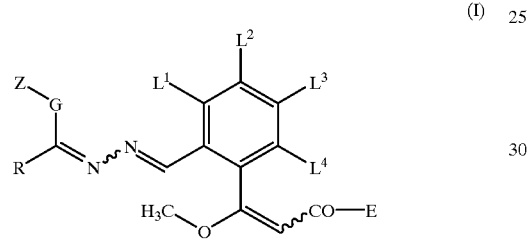

in which

E represents methoxy, ethoxy, $NH_2$ or $NH-CH_3$,

G represents a single bond or a grouping

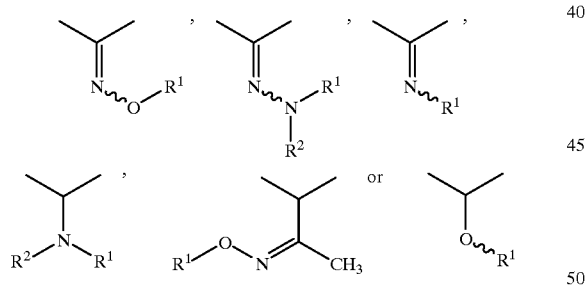

in which $R^1$ and $R^2$ are identical or different and independently of one another each represents optionally substituted alkyl, alkenyl, alkinyl, aryl, cycloalkyl, alkylcarbonyl or arylcarbonyl, R represents hydrogen, alkyl or in each case optionally substituted cycloalkyl or aryl, Z represents cyano, alkoxycarbonyl, alkoxy, cycloalkoxy or in each case optionally substituted alkyl, cycloalkyl, cycloalkylalkyl, aryl, or arylalkyl, and $L^1$, $L^2$, $L^3$ and $L^4$ are identical or different and independently of one another each represents hydrogen, halogen, cyano, nitro, in each case optionally halogen-substituted alkyl, alkoxy, alkylthio, alkylsulphinyl or alkylsulphonyl.

2. Compounds of the formula (I) according to claim 1, in which

E represents methoxy, ethoxy, $NH_2$ or $NH-CH_3$,

G represents a single bond,

R represents alkyl having 1 to 4 carbon atoms or represents cycloalkyl having 3 to 6 carbon atoms or phenyl, each of which is optionally mono- to tetrasubstituted by halogen or alkyl, Z represents cycloalkyl or cycloalkylalkyl having in each case 3 to 7 carbon atoms in the cycloalkyl moiety and 1 to 4 carbon atoms in the alkyl moiety and being in each case optionally mono- to tetrasubstituted by halogen or alkyl;

or represents aryl or arylalkyl having in each case 6 to 10 carbon atoms in the aryl moiety and 1 to 4 carbon atoms in the alkyl moiety and being in case optionally mono- to tetrasubstituted in the aryl moiety by identical or different substituents, where the possible substituents are selected from the list below:

halogen, cyano, nitro, amino, carbamoyl, thiocarbamoyl;

in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkoxycarbonyl, alkylaminocarbonyl, dialkylaminocarbonyl or arylalkylaminocarbonyl having 1 to 6 carbon atoms in the respective hydrocarbon chains;

cycloalkyl or cycloalkyloxy having in each case 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents from the group consisting of fluorine, chlorine, methyl, trifluoromethyl and ethyl;

phenoxy or phenylalkoxy having 1 to 4 carbon atoms in the alkyl moiety, each of which is optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms;

or a grouping

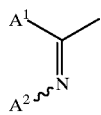

, in which
A¹ represents hydrogen or alkyl having 1 to 4 carbon atoms or cycloalkyl having 3 to 6 carbon atoms and
A² represents hydroxyl, amino, methylamino, methyl, phenyl, benzyl, alkoxy, alkylamino, dialkylamino having 1 to 4 carbon atoms in the respective alkyl chains and
L¹, L², L³ and L⁴ are identical or different and independently of one another each represents hydrogen, halogen, cyano, nitro, or alkyl, alkoxy, alkylthio, alkylsulphinyl or alkylsulphonyl having in each case 1 to 6 carbon atoms and being in each case optionally substituted by 1 to 5 halogen atoms.

3. Compounds of the formula (I) according to claim 1, in which
E represents methoxy, ethoxy, $NH_2$ or $NH-CH_3$,
G represents a grouping

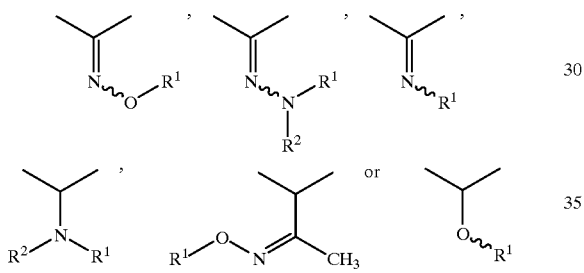

, in which
R¹ and R² are identical or different and independently of one another represent alkinyl having 2 to 6 carbon atoms, alkenyl having 2 to 6 carbon atoms or alkyl or alkylcarbonyl having 1 to 6 carbon atoms, each of which is optionally substituted by halogen or alkoxy having 1 to 4 carbon atoms, or represents cycloalkyl having 3 to 8 carbon atoms which is optionally substituted by halogen, alkyl or alkoxy having in each case 1 to 4 carbon atoms or represents phenyl, or phenylalkyl having optionally 1 to 4 carbon atoms in the alkyl moiety or phenylcarbonyl, each of which is optionally substituted in the phenyl moiety, where the substituents are selected from the list below:
halogen, cyano, nitro, alkyl, alkoxy, alkylthio, alkylsulphinyl or alkylsulphonyl having in each case 1 to 6 carbon atoms, halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case halogenoalkyl or halogenoalkyloxy having in each case 2 to 6 carbon atoms and 1 to 11 identical or different halogen atoms,
R represents alkyl having 1 to 4 carbon atoms or represents cycloalkyl having 3 to 6 carbon atoms or phenyl, each of which is optionally mono- to tetrasubstituted by halogen or alkyl, Z represents cyano, alkoxycarbonyl or alkoxy having in each case 1 to 4 carbon atoms in the alkyl moiety, cycloalkoxy having 5 or 6 carbon atoms, or
represents alkyl or halogenoalkyl having in each case 1 to 4 carbon atoms and being in each case optionally monosubstituted by cyano or alkoxy, or
represents cycloalkyl or cycloalkylalkyl having in each case 3 to 7 carbon atoms in the cycloalkyl moiety and 1 to 4 carbon atoms in the alkyl moiety and being in each case optionally mono- to tetrasubstituted by halogen or alkyl;
or represents aryl or arylalkyl having in each case 6 to 10 carbon atoms in the aryl moiety and 1 to 4 carbon atoms in the alkyl moiety and being in each case optionally mono- to tetrasubstituted in the aryl moiety by identical or different substituents, where the possible substituents are selected from the list below:
halogen, cyano, nitro, amino, carbamoyl, thiocarbamoyl;
in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 11 identical or different halogen atoms;
in each case straight-chain or branched alkylamino, dialkylamino, alkoxycarbonyl, alkylaminocarbonyl, dialkylaminocarbonyl or arylalkylaminocarbonyl having 1 to 6 carbon atoms in the respective hydrocarbon chains;
cycloalkyl or cycloalkyloxy having in each case 3 to 6 carbon atoms;
in each case doubly attached alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents from the group consisting of fluorine, chlorine, methyl, trifluoromethyl and ethyl;
phenoxy or phenylalkoxy having 1 to 4 carbon atoms in the alkyl moiety, each of which is optionally substituted by halogen, alkyl, alkoxy, alkylthio, alkylsulphinyl or alkylsulphonyl having 1 to 4 carbon atoms, halogenoalkoxy, halogenoalkylthio, halogenoalkylsulphinyl or halogenoalkylsulphonyl having 1 to 4 carbon atoms and 1 to 9 halogen atoms, or a grouping

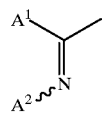

, in which
A¹ represents hydrogen or alkyl having 1 to 4 carbon atoms or cycloalkyl having 3 to 6 carbon atoms and
A² represents hydroxyl, amino, methylamino, methyl, phenyl, benzyl, alkoxy, alkylamino, dialkylamino having 1 to 4 carbon atoms in the respective alkyl chains and
$L^1$, $L^2$, $L^3$ and $L^4$ are identical or different and independently of one another each represents hydrogen, halogen, cyano, nitro, or alkyl, alkoxy, alkylthio, alkylsulphinyl or alkylsulphonyl having in each case 1 to 6 carbon atoms and being in each case optionally substituted by 1 to 5 halogen atoms.

4. Compounds of the formula (I) according to claim 1, in which
E represents methoxy, ethoxy, amino or methylamino,
G represents a single bond,
R represents methyl, ethyl, n- or i-propyl, or represents cyclopropyl, cyclobutyl, cyclopentyl or phenyl, each of which is optionally mono- to tetrasubstituted by fluorine, chlorine, methyl or ethyl;
Z represents cyclopentyl or cyclohexyl, each of which is optionally mono- to tetrasubstituted by fluorine, chlorine, methyl or ethyl; or represents benzyl, 1-phenylethyl or 2-phenylethyl, each of which is optionally mono- to tetrasubstituted by identical or different substituents, where the possible substituents are selected from the list below:
fluorine, chlorine, bromine, cyano, nitro, amino, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy; trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, methoxycarbonyl, ethoxycarbonyl, methylaminocarbonyl, ethylaminocarbonyl, dimethylaminocarbonyl, diethylaminocarbonyl, cyclopentyl, cyclohexyl, cyclopentyloxy, cyclohexyloxy, in each case doubly attached propanediyl, ethyleneoxy, methylenedioxy, ethylenedioxy, each of which is optionally mono- to tetrasubstituted by identical or different substituents from the group consisting of fluorine, chlorine, methyl and trifluoromethyl,
in each case optionally fluorine-, chlorine-, methyl-, trifluoromethyl- or methoxy-substituted phenoxy or benzyl, or a grouping

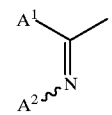

, where
A¹ represents hydrogen or methyl and
A² represents hydroxyl, methoxy, ethoxy, amino, methylamino, methyl, phenyl or benzyl, and
$L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

5. Compounds of the formula (I) according to claim 1, in which
E represents methoxy, ethoxy, amino or methylamino,
G represents a grouping

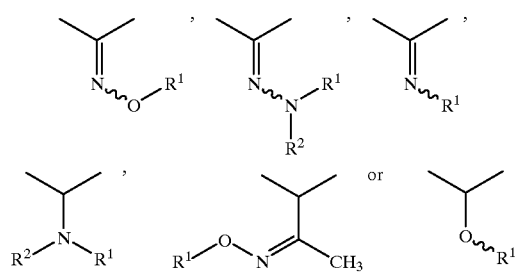

, in which
R¹ and R² are identical or different and independently of one another each represents in each case optionally fluorine-, chlorine- or methoxy-substituted methyl, ethyl, n- or i-propyl, n-, i-, s- or t-butyl, acetyl, propionyl, allyl, crotonyl, propargyl or represents optionally fluorine-, chlorine-, methyl- or methoxy-substituted cyclopentyl or cyclohexyl or represents phenyl, benzyl, or benzoyl, each of which is optionally substituted in the phenyl moiety, where the substituents are selected from the list below:
fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl,
R represents methyl, ethyl, n- or i-propyl, or represents cyclopropyl, cyclobutyl, cyclopentyl or phenyl, each of which is optionally mono- to tetrasubstituted by fluorine, chlorine, methyl or ethyl, Z represents cyano, methoxycarbonyl, ethoxycarbonyl, methyl, ethyl, n- or i-propyl, n-, i-, s- or t-butyl, trifluoromethyl, trifluoroethyl, methoxy, ethoxy, n- or i-propoxy, cyclopentyloxy or cyclohexyloxy or represents cyclopentyl or cyclohexyl, each of which is optionally mono- to tetrasubstituted by fluorine, chlorine, methyl or ethyl; or represents benzyl, 1-phenylethyl or 2-phenylethyl, each of which is optionally mono- to tetrasubstituted by identical or different substituents, where the possible substituents are selected from the list below:

fluorine, chlorine, bromine, cyano, nitro, amino, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy; trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, methoxycarbonyl, ethoxycarbonyl, methylaminocarbonyl, ethylaminocarbonyl, dimethylaminocarbonyl, diethylaminocarbonyl, cyclopentyl, cyclohexyl, cyclopentyloxy, cyclohexyloxy, in each case doubly attached propanediyl, ethyleneoxy, methylenedioxy, ethylenedioxy, each of which is optionally mono- to tetrasubstituted by identical or different substituents from the group consisting of fluorine, chlorine, methyl and trifluoromethyl in each case optionally fluorine-, chlorine-, methyl-, trifluoromethyl- or methoxy-substituted phenoxy or benzyl, or a grouping

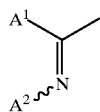

, where

A$^1$ represents hydrogen or methyl and

A$^2$ represents hydroxyl, methoxy, ethoxy, amino, methylamino, methyl, phenyl or benzyl, and L$^1$, L$^2$, L$^3$ and L$^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

6. The compounds of claim 1 wherein E is methoxy, R is methyl or cyclopropyl L$^1$, L$^2$, L$^3$ and L$^4$ are identical or different and independently dependently of one another each represents hydrogen or methyl.

7. The compounds of claim 1, wherein compound is of the formula:

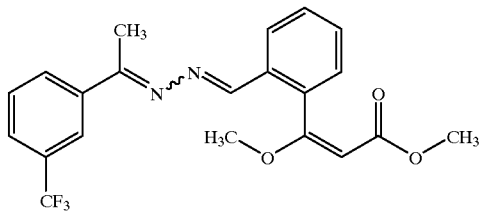

8. Process for preparing compounds of the formula (I) as defined in claim 1, characterized in that hydrazones of the formula (II)

(II)

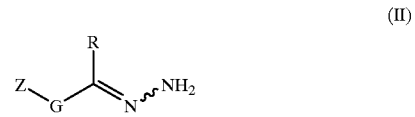

in which

G, R and Z are as defined in claim 1 are reacted with an aldehyde of the general formula (III)

(III)

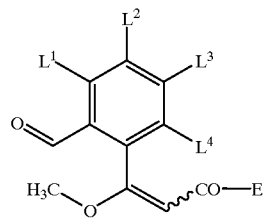

in which

E, L$^1$, L$^2$, L$^3$ and L$^4$ are as defined in claim 1, if appropriate in the presence of a diluent and if appropriate in the presence of a catalyst.

9. Amicrobicidal composition comprising an effective amount of at least one compound of the formula (I) according to claim 1 in admixture with an inert diluent.

10. Method for controlling undesirable microorganisms, characterized in that compounds of the formula (I)compositions according to claim 1 are allowed to act on microorganisms and/or their habitat.

* * * * *